US006117342A

United States Patent [19]

Schnell et al.

[11] Patent Number: 6,117,342

[45] **Date of Patent: *Sep. 12, 2000**

[54] BUBBLE TRAP WITH DIRECTED HORIZONTAL FLOW AND METHOD OF USING

[75] Inventors: William J. Schnell, Libertyville, Ill.; David S. Utterberg, Seattle, Wash.

[73] Assignee: Medisystems Technology Corporation, Las Vegas, Nev.

[ * ] Notice: This patent issued on a continued prosecution application filed under 37 CFR 1.53(d), and is subject to the twenty year patent term provisions of 35 U.S.C. 154(a)(2).

[21] Appl. No.: 09/207,229

[22] Filed: Dec. 8, 1998

Related U.S. Application Data

[63] Continuation of application No. 08/755,806, Nov. 26, 1996, abandoned.

[51] Int. Cl.$^7$ .............................. B01D 19/00; A61M 5/36

[52] U.S. Cl. .............................. 210/800; 95/241; 95/260; 96/179; 96/219; 210/188; 210/436; 210/801; 604/4; 604/122

[58] Field of Search .............................. 96/155, 176, 179, 96/219, 220; 210/188, 436, 456, 472, 767, 800, 801; 604/4, 630, 122, 123; 422/94–98; 95/241, 243, 260

[56] References Cited

U.S. PATENT DOCUMENTS

| | | | |
|---|---|---|---|
| 3,287,885 | 11/1966 | Sommer . | |
| 3,342,019 | 9/1967 | Smythe . | |
| 3,527,572 | 9/1970 | Urkiewicz . | |
| 3,795,088 | 3/1974 | Esmond . | |
| 3,908,653 | 9/1975 | Kettering . | |
| 3,996,027 | 12/1976 | Schnell et al. . | |
| 4,031,891 | 6/1977 | Jess . | |
| 4,048,995 | 9/1977 | Mittleman . | |
| 4,137,160 | 1/1979 | Ebling et al. . | |
| 4,149,860 | 4/1979 | Kulik . | |
| 4,293,413 | 10/1981 | Schnell et al. | 210/188 |
| 4,311,137 | 1/1982 | Gerard et al. . | |
| 4,345,999 | 8/1982 | Sigdell et al. . | |
| 4,368,118 | 1/1983 | Siposs | 210/436 |
| 4,493,705 | 1/1985 | Gordon et al. | 604/122 |
| 4,531,937 | 7/1985 | Yates | 604/122 |
| 4,568,333 | 2/1986 | Sawyer et al. | 604/122 |
| 4,622,032 | 11/1986 | Katsura et al. . | |
| 4,643,713 | 2/1987 | Viitala . | |
| 4,666,598 | 5/1987 | Heath et al. . | |
| 4,681,606 | 7/1987 | Swan, Jr. et al. . | |
| 4,722,725 | 2/1988 | Sawyer et al. | 604/122 |
| 4,722,731 | 2/1988 | Vailancourt | 604/122 |
| 4,734,269 | 3/1988 | Clarke et al. . | |
| 5,061,236 | 10/1991 | Sutherland et al. . | |

(List continued on next page.)

FOREIGN PATENT DOCUMENTS

| | | |
|---|---|---|
| 0 058 325 | 8/1982 | European Pat. Off. . |
| 0 318 993 | 6/1989 | European Pat. Off. . |
| 0 350 675 | 1/1990 | European Pat. Off. . |
| 0 587 251 A1 | 3/1994 | European Pat. Off. . |
| 1 408 319 | 10/1975 | United Kingdom . |
| 1 554 810 | 4/1979 | United Kingdom . |

OTHER PUBLICATIONS

Medisystems Sales Drawing of ReadySet™ Blood Tubing, Mar., 1993.

*Primary Examiner*—Joseph W. Drodge
*Attorney, Agent, or Firm*—Garrettson Ellis Seyfarth, Shaw

[57] ABSTRACT

An extracorporeal, flow-through bubble trap for blood lines having improved capabilities at high flow rates and with smaller bubbles. The bubble trap comprises a chamber-defining wall, plus a blood inlet and a blood outlet, each extending through the wall to communicate with the interior of the chamber. The blood outlet connects with the chamber interior adjacent the bottom thereof. The chamber interior has a height that is less than 1.6 times the longest horizontal dimension of the chamber interior. As a result of this, blood flow in the bubble trap chamber is substantially horizontal.

36 Claims, 2 Drawing Sheets

U.S. PATENT DOCUMENTS

| | | | |
|---|---|---|---|
| 5,061,365 | 10/1991 | Utterberg . | |
| 5,204,000 | 4/1993 | Stedman et al. . | |
| 5,228,889 | 7/1993 | Cortial et al. . | |
| 5,328,461 | 7/1994 | Utterberg . | |
| 5,356,376 | 10/1994 | Milijasevic et al. | 604/30 |
| 5,358,481 | 10/1994 | Todd et al. | 604/4 |
| 5,411,705 | 5/1995 | Thor et al. . | |
| 5,429,595 | 7/1995 | Wright, Jr. et al. . | |
| 5,441,636 | 8/1995 | Chevallet et al. | 210/232 |
| 5,503,801 | 4/1996 | Brugger | 210/436 |
| 5,520,640 | 5/1996 | Utterberg . | |
| 5,591,251 | 1/1997 | Brugger . | |
| 5,683,355 | 11/1997 | Fini et al. . | |
| 5,769,815 | 6/1998 | Utterberg . | |

BUBBLE TRAP WITH DIRECTED HORIZONTAL FLOW AND METHOD OF USING

CROSS REFERENCE TO RELATED APPLICATION

This is a continuation of application Ser. No. 08/755,806 filed Nov. 26, 1996, now abandoned.

BACKGROUND OF THE INVENTION

Bubble traps used in blood lines for hemodialysis or the like conventionally comprise a typically rigid or semi-rigid tube in which a blood inlet is provided to convey blood into the top of the chamber, while a blood outlet draws blood from the bottom of the chamber. Bubbles then are given the opportunity to rise to the top of the chamber so that the blood in the bottom of the chamber, which is withdrawn to pass through another portion of the blood set, is relatively free of bubbles, since they migrate to the top of the chamber.

See also Utterberg U.S. Pat. Nos. 5,328,461 and 5,520,640 as other examples of bubble traps for blood lines known to the prior art.

Typically, such bubble traps are higher than they are wide, to provide a deep, vertical chamber for the blood so that bubbles are kept away from the bottom of the chamber, from which the blood is being withdrawn. Typically, the prior art bubble traps have chambers with a vertical height that is more than twice their width. The height of the chambers of the prior art, coupled with the buoyancy of the incoming bubbles, is intended to counteract the downward bulk fluid flow of blood in the chamber toward the bottom outlet.

The inlets of the prior art blood chambers are variably positioned, the idea being that the blood entering into such inlets, and the bubbles contained in the blood, will initially stay in an upper portion of the chamber so that the bubbles have time to migrate upwardly through a liquid level to a gas space at the top of the chamber. Some inlets are vertically oriented, extending downwardly from the top of the chamber. Because of the height of the chamber, inflowing blood stops moving downwardly before the bubbles contained in it can be caught in the outlet flow. Other inlets of the prior art are vertically oriented in the bottom of the chamber, to propel the inlet blood upwardly toward the chamber top. Other inlets are horizontally oriented in the side of the chamber, so that the inlet flow must horizontally cross the downward flow of the bulk blood in the chamber, moving to an opposite sidewall where it is turned upwardly. This raises the possibility of bubbles being entrained in the downward flow before they are turned upwardly to reach the intended air space.

The bubble trapping principles of the prior art are effective with large, buoyant bubbles, typically having a volume greater than 50 microliters, and at relatively low blood flow rates of less than 300 ml. per minute. Blood chambers for trapping bubbles typically have volumes of about 15–25 ml. The buoyancy of the bubbles urges them to the surface at a velocity greater than the downward velocity of the bulk flow of the fluid in the bubble trap.

However, such bubble traps are increasingly ineffective as bubbles get smaller, and/or as flow rates increase. Modern dialysis techniques often require blood flow rates exceeding 450 ml. per minute, which raises the risk that bubbles can get through bubble traps of the prior art.

To accommodate such higher flows, the volumes of some designs of prior art bubble traps have been increased. However, this is distinctly undesirable, since that increases the priming volume of the set. It is highly desirable to keep the priming volume of any blood set low, since it is important to minimize the amount of blood removed from a patient at any one time during a blood treatment procedure such as dialysis.

Furthermore, another problem of prior art bubble traps, particularly those with the upwardly oriented inlets, is that they may require a flow diverter, to prevent blood at high flow rate from bursting through the blood-gas interface in a geyser-like action, which causes foaming of the blood and consequent clotting in the chamber. A typical blood flow diverter comprises an indentation in the wall of the bubble trap, to force the upwardly moving stream of inlet blood into a more horizontal flow, to prevent such geyser-like action. However, the diverter itself is not deemed desirable, and may result in an increased number of bubbles to be driven down toward the bottom outlet and thus to pass out of the bubble trap, contrary to that which was intended.

In accordance with this invention, solutions to the above technical problems are provided, resulting in an improved flow-through bubble trap for blood lines or the like, which is capable of processing blood at high flow rates of 450 ml. per minute and greater, while still retaining a low chamber interior volume.

DESCRIPTION OF THE INVENTION

By this invention, an extracorporeal, flow-through bubble trap for fluid lines comprises: a chamber-defining wall, a blood inlet, and a blood outlet, each of which extends through the wall to communicate with the interior of the chamber. The blood outlet connects with the chamber interior adjacent the bottom thereof, so that blood is drawn from the bottom of the chamber out of the outlet. The chamber interior has a height that is less than 1.6 times the longest horizontal dimension of the chamber interior, and preferably no more than 1.2 times. Also, the blood outlet and blood inlet are typically horizontally separated at their closest points by at least about 8 mm., most preferably at least 10 mm.

As a result of this, blood flow in the bubble trap is substantially horizontal, contrary to the blood chambers of the prior art, which are taller than they are wide. Also, since the outlet and inlet are preferably spaced from each other by at least about 8 mm., there is little or no chance of crossover of inlet blood, with included bubbles, passing immediately from the inlet to the outlet and carrying the bubbles with it. This can be further assured by causing the blood inlet to direct blood flow into the chamber only in a direction or directions facing away from the blood outlet. The blood outlet may receive blood only from a side facing away from the blood inlet.

It is also preferred for the volume of the chamber interior to be no more than about 25 cc., to contribute to a low priming volume of the set to which the bubble trap belongs.

It is also preferred for the height of the chamber interior to be no more than the longest horizontal dimension of the chamber interior, with the result that the blood flow within the chamber is primarily horizontal.

The bubble trap of this invention may have a blood inlet which comprises a tube that extends into the chamber interior at a position that is spaced at least 4 mm., and preferably at least 5 mm., from any chamber sidewall. An advantage achieved by this is that any foam bridges formed from blood and extending between such a tube and the sidewall are strongly suppressed by having the tube at such a distance from the sidewall, rather than closer as has been customary in the prior art. Such foam bridges formed from swirling, turbulent blood in the bubble trap promote clotting.

Further, the blood inlet tube may preferably extend between the top and bottom of the chamber, and may be in contact with both the top and the bottom, to provide internal support for the chamber wall. The blood outlet may also comprise a similar supporting tube extending between the top and bottom of the chamber. Blood may flow between the chamber and the interior of the inlet and outlet tubes either by a side aperture formed in the respective tubes, or by a recess defined in the inner surface of the chamber wall, which provides space for blood to flow into or out of the end of the inlet and/or outlet tubes around one portion of the annular tube end, while another portion of the annular tube end may press against the bottom wall of the housing.

It is also preferred for the flow-through bubble trap of this invention to comprise a chamber-defining wall which defines an interior chamber comprising an upper chamber portion and a lower chamber portion. The upper chamber portion has a greater horizontal area than the lower chamber portion, preferably at least three times greater, with the lower chamber portion being typically positioned toward one side of the upper chamber portion. The upper chamber portion has a height that is less than 1.6 times the longest horizontal dimension of the upper chamber portion (and preferably 1.2 times). Most preferably, the height of the upper chamber portion is less than the longest horizontal dimension thereof.

A blood outlet is positioned to communicate with a bottom end portion of the lower chamber portion. The blood inlet is positioned to release flowing blood into the upper chamber portion, preferably at a position remote from the lower chamber portion.

It is also preferred for a filter to be carried near the junction of the upper and lower chamber portions, to filter blood flowing between the upper chamber portion and the lower chamber portion. The lower chamber portion may be defined by a cylindrical portion of the chamber-defining wall, so that it can fit into conventional receptacles of air/form detection apparatus of a type conventionally used in hemodialysis and other blood handling processes. The lower chamber portion may have a horizontal, cross-sectional area that is no more than one third the horizontal, cross-sectional area of the upper chamber portion.

In this embodiment also, it is preferred for the volume of the upper chamber portion to be no more than about 25 cc. Also, the blood inlet preferably directs blood flow into the chamber in a direction facing away from the lower chamber portion, so that bubbles have time to rise to an uppermost portion of the chamber before the blood reaches the lower chamber portion. Also, as before, the blood inlet preferably comprises a tube that extends into the chamber interior at a position that is spaced at least 4 mm. and preferably 5 mm. from any chamber sidewall, with the tube preferably extending between the top and the bottom of the bubble trap. Also, the inlet tube may have a side aperture or an exposed end to deliver inlet blood preferably in a direction away from the outlet port and substantially spaced below the upper surface of the blood in the upper chamber portion, so that blood at a high flow rate can pass through the upper blood chamber portion without splashing, spattering, or geysering of blood upwardly from the upper blood surface.

The bubble trap of all these inventive chambers may be operated with a substantial air space at the top of the chamber to define a blood level below the top of the chamber. However, due to the enhanced horizontal flow characteristics of the blood in the bubble trap of this invention, and the unique flow and mixing pattern that is provided within the chamber, it becomes possible to operate the bubble trap of this invention with the chamber being substantially filled with blood, so that the surface area of blood exposed to air can be reduced. This has the effect of reducing the tendency of clotting.

When chambers of the prior art are filled to the top so as to substantially lack an air space, the blood at the top of such prior art chambers tends to be stagnant during operation, resulting in enhanced clotting. Thus, it has been generally necessary in prior art practice to ensure the presence of a substantial air space above the blood level. By this invention, that is no longer necessary.

It is necessary to take steps to ensure that the blood does not get into the pressure monitor line or any other access line at the top of the bubble trap. This can be accomplished by the placement of a hydrophobic filer at the point where the line communicates with the bubble trap chamber, or by careful filling of the chamber first with saline for priming, and then with blood, keeping track of the various pressures under which the chamber will operate, which of course are generated by varying flow rates through the chamber. However, by this invention, the area of contact between the blood and air can be greatly reduced on a long term basis through the dialysis process. Since the chamber may be substantially completely filled with blood, but for the relatively few bubbles collected during the blood treatment process. Much of the horizontal upper surface of the blood may be in contact with the top chamber wall.

The bubble traps of this invention may be of generally oval cross section, either overall, or in the upper chamber portion when a lower chamber portion is present. The horizontal dimensions of such an oval cross section may be approximately 22 by 44 mm., with the height of the chamber comprising 30 mm. in one embodiment. This creates a very low priming volume when compared with long, vertical chambers designed for high flows. When a lower chamber portion is present, it also may preferably have a height of about 30 mm.

DESCRIPTION OF SPECIFIC EMBODIMENTS

Figure 1:
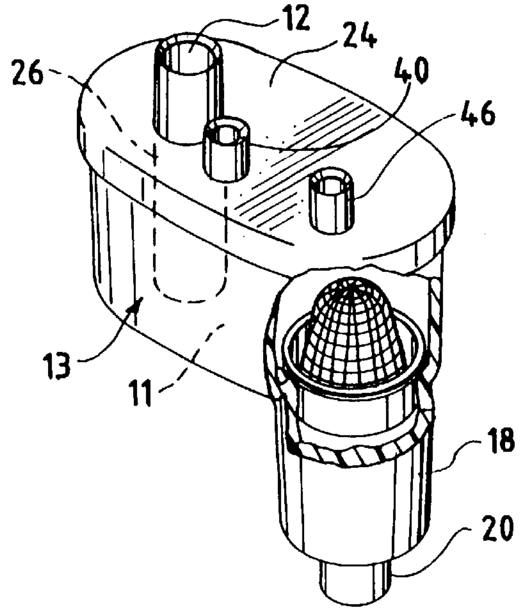
FIG. 1 is a perspective view of one embodiment of the chamber of this invention.

Referring to FIGS. 1 through 4, a bubble trap 10 is shown, being suitable for use to replace the bubble traps of conventional arterial or venous hemodialysis sets, as well as other blood handling sets, or any conduits where a small, highly effective degassing chamber is desired. Bubble trap 10 is of the flow-through type, since the blood flows into chamber 11 of bubble trap through inlet port 12, and out again through outlet port 20. Chamber 11 is surrounded by wall on all sides thereof.

Chamber 11 comprises an upper chamber portion and a lower chamber portion 16, lower chamber portion being defined by a cylindrical, transparent portion 18 wall 13, proportioned to fit into a conventional air/foam detector. Typically all of wall 13 is transparent. Upper wall 24 may comprise a separately molded lid, if desired, which is peripherally bonded to chamber 11 to become part of wall 13.

Blood flow outlet 20 is then defined at the tom of lower chamber portion 16. Conventional set tubing 13, 15 respectively connects to inlet and outlet 12, 20.

Upper chamber portion 14 is dimensioned to have a height 22 that is less than the maximum width 23 of upper chamber portion 14.

Lower chamber portion 16 can be seen to be positioned adjacent to one side of upper chamber portion 14 at a position horizontally remote, typically by at least 8 mm. from the nearest portion of blood inlet 12.

Blood inlet 12 communicates with an interior tube 26 that extends through upper wall portion 24 of the bubble trap and extends through chamber 14 into contact with or nearly adjacent with lower wall portion 24 of the 26 defines a cut away side portion 30 of its wall, facing away from lower chamber portion 16, so that inflowing blood as illustrated by arrow 32 enters through inlet 12 and tube 26 in a vertical flow pattern, and is turned at the end of tube 26 by wall portion 28 into a horizontal flow through side aperture 30, away from second chamber portion 16. Tube 26 is also spaced at least 5 mm. from the nearest sidewall portion 34 of bubble trap 10, to avoid the undesirable creation of a bridge of blood/foam between tube 26 and wall 34 or vertical annular member 35, which forms a lid or cover member with upper wall portion 24 that closes the chamber.

Figure 2:
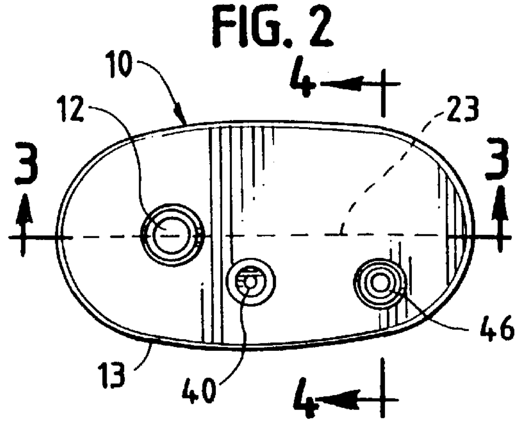
FIG. 2 is a plan view of the chamber of FIG. 1.

An air space 36 above the blood level 38 is shown as one normal condition for operative blood flow through the bubble trap. However, as previously described, it is also possible to operate this bubble trap with the blood level substantially in contact with the undersurface of upper wall portion 24, to minimize the area of the blood-air interface. By the particular design of bubble trap disclosed in this invention, a distinct, generally horizontal, swirling flow pattern for the blood can be provided, where blood next to the undersurface of upper wall portion 24 is not stagnant, but participates in a good flow, to suppress blood clotting. Collected air bubbles may be periodically removed through an access port 46 (FIG. 2).

Tubing connector 40 is conventionally provided to permit access to a tube that leads to a pressure sensor in conventional manner, or an additive tube for the conventional addition of saline solution or desired medications.

The bubble trap also defines a basket-type filter 44 which is positioned adjacent to the junction between the upper and lower chamber portions 14, 16, leaving open the majority of lower chamber portion 16. Thus, the cylindrical wall portion 18 of the lower chamber portion 16 may be inserted into a conventional air-foam detector, with filter 44 being out of the way so that air and foam can be detected underneath it in the conventional manner during a dialysis procedure. Annular securance ring 45 of filter 44 may be conventionally secured in the position shown. The shorter, lower chamber that results from this "mid-chamber" filter has reduced priming volume than a normal vertical chamber with the filter at the bottom and with the ultrasound air/foam sensing signal passing above the filter.

Because of the primarily horizontal flow of blood in upper chamber 14, air bubbles in the blood are given more opportunity to migrate upwardly to the top of the chamber than in other designs of bubble trap, where the bubbles have to rise against a downward flowing current of blood. It can be seen that there is no major downward flow of the blood in chamber 14 in the left half of the chamber (FIG. 3), giving the bubbles extra opportunity to rise to air space 36 despite the fact that the volume of upper chamber 14 is preferably less than 25 cc., (and the volume of lower chamber 16 is correspondingly low). It is possible to run high flow rates of blood, of 450 ml. per minute and greater, while still reliably and effectively separating out essentially all bubbles, so that the outflow of blood through outlet port 20 is substantially bubble free.

Figure 3:
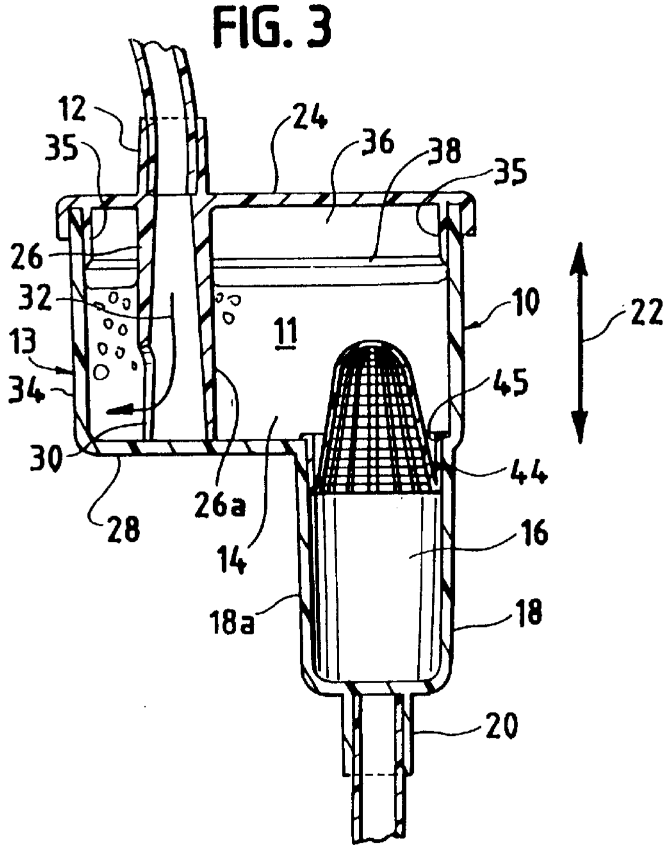
FIG. 3 is a vertical section of the chamber of FIGS. 2, taken along line 3—3 of FIG. 2.
Figure 4:
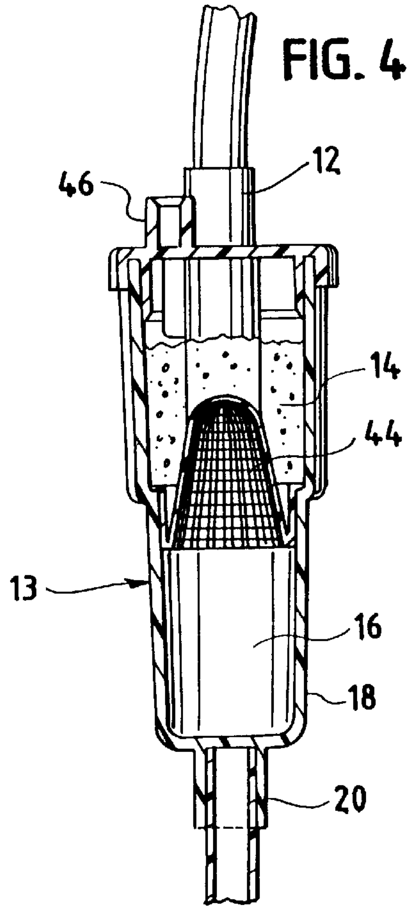
FIG. 4 is a vertical sectional view taken along line 4—4 of FIG. 2.

Referring to FIG. 3, the right hand wall portion **26*a* of tube 26 is horizontally separated by more than 8 mm. from the left hand wall portion 18*a*, which surrounds lower chamber 16**.

Thus, a uniquely effective, high flow capacity bubble trap is provided, being typically used in extracorporeal blood sets, but also suitable for other desirable uses of fluid handling.

Figure 5:
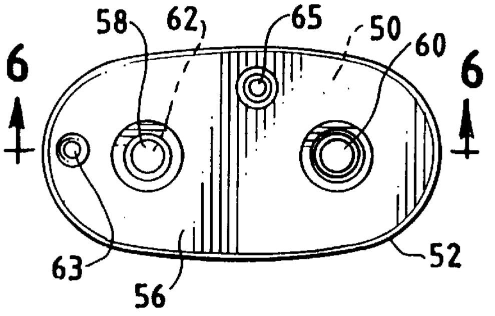
FIG. 5 is a plan view of another embodiment of bubble trap in accordance with this invention.
Figure 6:
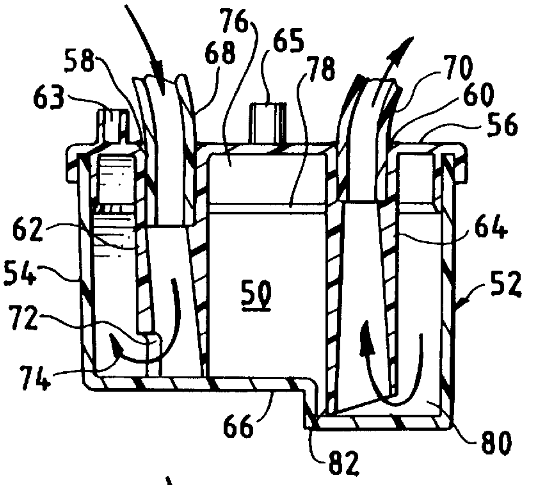
FIG. 6 is a vertical sectional view taken along line 6—6 of FIG. 5.

Referring to FIGS. 5 and 6, another embodiment of a bubble trap is disclosed, comprising a chamber 50 which is defined on all sides by a chamber-defining wall 52, and has a volume of less than 25 cc. Wall 52 may, in turn, be defined by a cup 54 which is closed with a cap 56. Cap 56, in turn, is a molded structure that also integrally defines inlet port 58, outlet port 60, and internal tubes 62, 64 that serve to convey the blood into the chamber interior. Both tubes 62, 64 are proportioned so that their lower ends engage or are at least adjacent the inner wall of chamber bottom wall portion 66. Each of flow tubes 62, 64 have enlarged inlet port openings to respectively receive flexible blood tubing or pump segment tubing sections 68, 70 as part of an extracorporeal blood set, which may otherwise be of conventional design. The above is similar in part to the previous embodiment.

Tube 62 defines a side opening 72 comprising typically one-half or less of the circumference of tube 62 and facing away from tube 64. Thus, blood flow from flexible tubing 68 enters inlet 58, and passes downwardly through tube 62 until it is turned into horizontal flow by bottom wall portion 66, to flow out of aperture 72 in a generally horizontal flow pattern as indicated by arrow 74. Because chamber 50, defined by wall 52, is wider in at least one horizontal dimension than it is in the vertical dimension, the flow of blood is primarily horizontal. This makes it possible for bubbles to rise to air space 76 above blood level 78, without encountering a net downward flow of the blood in the left hand majority of chamber 50.

The bottom wall 66 defined by cup 54 further carries an internal recess 80. Tube 64 has a slanted end so that only a portion of the circumference of the end 82 of tube 64 is actually in contact with bottom wall portion 66. Typically, this portion of wall-contacting tube end may comprise less than one-half of the circumference of tube 64. Thus, outflowing blood passes through recess 80, around the end of tube 64 and into the bore thereof, to exit through outlet port 60 into flexible blood tubing 70, and on through the conventional extracorporeal blood set to which the bubble trap is attached.

Cap 56 may also carry one or more access ports 63, which may be a needle injection site, or may connect to tubing which carries a needle injection site, or which may connect to saline solution, additional medication, or the like. Port 65 (FIG. 5) may connect to a pressure monitor line of conventional design and purpose.

Here also, it is possible to raise blood level 78 into substantial contact with the undersurface of cap 56, to minimize the gas/blood interface area, which has the desirable characteristic of suppressing clotting of the blood. This can be accomplished with suppressed clotting at high flow rates, and even at low flow rates of 150 ml. per minute in the bubble trap of this invention because of the unique, swirling flow characteristics that prevent a stagnant area of blood from forming in the area immediately underneath cap 56. Also, at high flow rates in excess of 450 ml., the bubble trap of FIGS. 5 and 6 operates effectively to remove bubbles, even though the volume of chamber 50 may be on the order of 20 ml.

Figure 7:
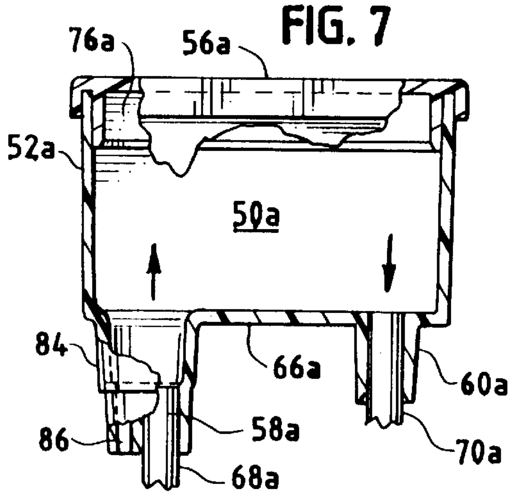
FIGS. 7, 8, and 9 are vertical sectional views of other embodiments of bubble trap in accordance with this invention.

Referring to FIG. 7, another embodiment of bubble trap is shown, similar to the embodiment of FIGS. 5 and 6 except as otherwise described herein. Chamber 50*a* is defined by sidewall 52*a*, and has preferably less than a 25 cc. volume. Chamber 50*a* comprises an inlet port 58*a* which passes through bottom wall 66*a* of the chamber, being defined by fitting 84.

Fitting 84 also defines another pair of inlet ports 86 (one behind the other) which may connect with outer inlet tubing that, in turn, connect a source of saline solution, heparin, or the like. The chamber of FIG. 7 also defines an outlet port 60*a* extending through bottom wall 66*a*. The respective inlet and outlet ports are connected to flexible tubing 68*a*, 70*a* for conventional incorporation into an arterial or a venous set.

In this embodiment, the maximum width of chamber 50*a* remains greater than the height of the chamber. The horizontal cross section of the chamber of FIG. 7 is the same as that shown in FIG. 5. Accordingly, while blood flow can enter through the chamber 50*a* bottom vertically upwardly, the flow within the chamber remains primarily horizontal. Bubbles are expelled upwardly from inlet 58*a* to air space 76*a* in a manner similar to the previous embodiment. Then, the primarily horizontal flow of blood to the bottom outlet 60*a* gives residual air bubbles the opportunity to rise toward air space 76*a* so that bubble-free fluid only passes through outlet port 60*a*.

Figure 8:
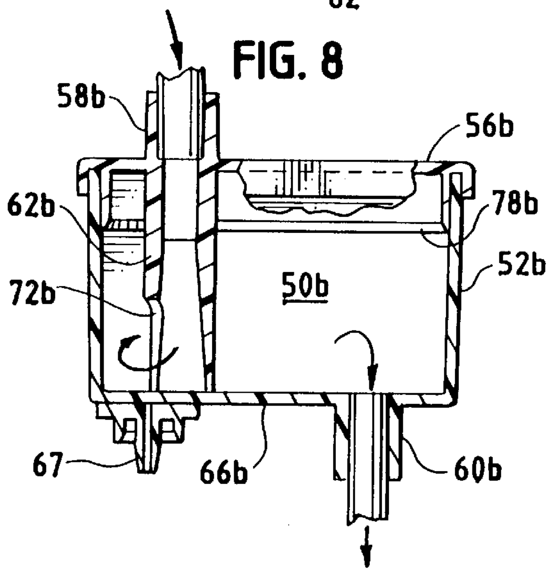

Referring to the bubble trap of FIG. 8, chamber 50*b* is defined by a sidewall 52*b*, which is of similar design to sidewall 52 of FIG. 6, having a lid or cover 56*b* as in the previous embodiments.

Blood entry port 58*b* enters through the top wall 56*b* in this embodiment, having a tube 62*b* that extends the height of chamber 50*b*, and has a side aperture 72*b* in the manner of the FIG. 6 embodiment, to place blood well under the surface 78*b* of blood in the chamber for the avoidance of geysering and spattering.

Blood outlet 60*b* is positioned to extend directly through bottom wall 66*b* as in the embodiment of FIG. 7.

Thus, blood may enter chamber 50*b* in the manner of the FIG. 6 embodiment, but it exits chamber 50*b* in the manner of the FIG. 7 embodiment. Because of the proportions of chamber 50*b*, longer in its longest horizontal dimension than it is high, the excellent bubble removal characteristics of this invention are achieved. FIG. 5 represents a horizontal cross section of FIG. 8 as well as that of the previous embodiments of FIGS. 6 and 7.

This chamber also has a preferable volume of less than 25 cc. Also, bottom port 67 can connect with tubing that communicates with a heparin source, for example, or saline solution.

Each of the chambers of FIGS. 6–9 can operate with the flow through them being in the opposite direction; i.e., outlet ports become the inlet ports, while the inlet ports become the outlet ports. In either case, effective removal of bubbles takes place from fluids.

Figure 9:
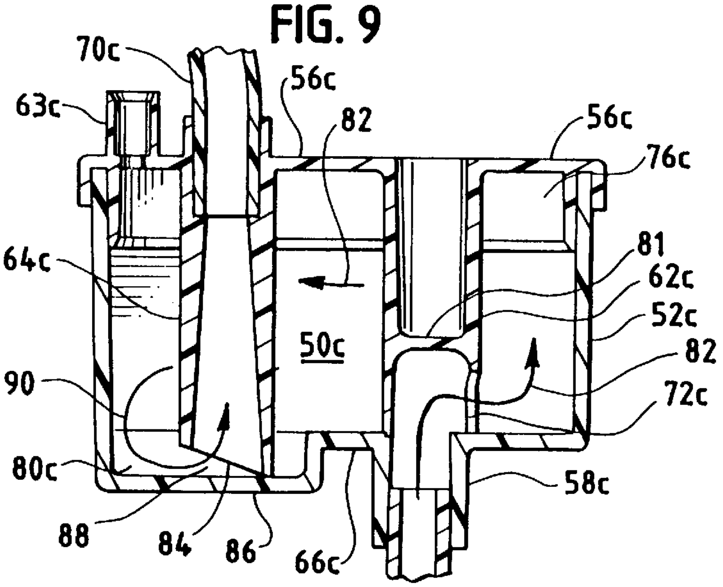

Referring to the bubble trap of FIG. 9, chamber 50*c* is defined by a sidewall 52*c*, which is of similar design to sidewall 52 of FIG. 6, having a lid or cover 56*c* as in previous embodiments.

Blood entry port 58*c* enters through the bottom wall 66*c* in this embodiment. A blood entry tube 62*c* is present as in previous embodiments, defining an internal entry side port 72*c* at or near the bottom of chamber 50*c*, as in previous embodiments. However, as a difference from previous embodiments, tube 62*c* has an internal wall 81, positioned so that all of the entering blood goes into chamber 50*c* through side aperture 72*c*. Tube 62*c* is surrounded by chamber 50*c* in a manner similar to tube 62, surrounded by chamber 50, in FIGS. 5–6.

Thus, as in previous embodiments, the entering blood passes primarily in a horizontal direction as shown by arrow 82, which facilitates the upward rise of bubbles into an air space 76*c* or, if no air space is used, to the undersurface of top wall 56*c*.

Outlet tube 64*c* is also provided, having a bevelled end 84, a minor portion of which rests against the bottom wall 86 of recess 80*c* so that a space 88 is provided for blood flow from chamber 50*c* and recess 80*c* into outlet tube 64*c*, as shown by arrow 90. Outlet tube 64*c* connects to flexible tube 70*c*, which preferably may be a peristaltic pumping segment.

Thus, it can be seen that bubble free blood passes through outlet tube 64*c* and into flexible set tubing 70*c* in a manner similar to that of the previous embodiments.

Access port 63*c*, similar to port 63 of FIG. 6, can also be provided for similar purposes.

The above has been offered for illustrative purposes only, and is not intended to limit the scope of the invention of this application, which is as defined in the claims below.

That which is claimed:

1. An extracorporeal, flow-through bubble trap for fluid flow lines, which comprises: a chamber-defining wall; a flow inlet and a flow outlet, each extending through said wall to communicate with the interior of said chamber, said flow inlet comprising a tube within the chamber that extends from the top to the bottom of the chamber, said tube having a flow impermeable wall and a side aperture connecting with said chamber interior adjacent the bottom thereof, said chamber interior having a height that is less than 1.6 times the longest horizontal dimension of said chamber interior, whereby fluid flow in the bubble trap chamber is substantially horizontal, said flow inlet directing fluid flow into said chamber exclusively in directions facing horizontally away from said flow outlet, in which said flow outlet and inlet are horizontally separated at their closest points by at least about 8 mm.

2. The bubble trap of claim 1 in which the volume of said chamber interior is no more than about 25 cc.

3. The bubble trap of claim 1 in which the height of the chamber interior is no more than the longest horizontal dimension of said chamber interior, whereby said fluid flow in the chamber is primarily horizontal.

4. The bubble trap of claim 1 in which the flow outlet and inlet are horizontally separated at their closest points by at least about 8 mm.

5. The bubble trap of claim 1 in which said flow inlet comprises a tube that extends into said chamber interior at a position that is spaced at least 4 mm. from any chamber side wall.

6. The bubble trap of claim 1, said side aperture of the flow inlet being positioned adjacent to a bottom wall of said bubble trap.

7. A tubular set for conveying blood between a patient and a blood treatment apparatus, said set comprising the flow-through bubble trap of claim 1.

8. An extracorporeal, flow-through bubble trap for bloodlines, which comprises: a chamber-defining wall which defines an interior comprising an upper chamber portion and a lower chamber portion, said upper chamber portion having a greater horizontal area than said lower chamber portion, said upper chamber portion having a height that is less than 1.6 times the longest horizontal dimension of said upper chamber portion, said lower chamber portion being positioned toward one side of said upper chamber portion; a blood outlet positioned to communicate with a bottom end portion of said lower chamber portion; and a blood inlet comprising a tube within said chamber that extends from the top to the bottom of said chamber, said tube having a fluid impermeable wall and a side aperture positioned and facing remotely from said lower chamber portion to horizontally release flowing blood into said upper chamber portion in a direction facing away from said lower chamber portion.

9. The bubble trap of claim 8 in which a filter is carried near the junction of the upper and lower chamber portions, to filter blood flowing between said upper chamber portion and said lower chamber portion.

10. The bubble trap of claim 8 in which the volume of said upper chamber portion is no more than about 25 cc.

11. The bubble trap of claim 8 in which the lower chamber portion has a cylindrical, outer, transparent wall.

12. The bubble trap of claim 8 in which said lower chamber portion has a horizontal cross-sectional area that is no more than one-third of the horizontal cross-sectional area of the upper chamber portion.

13. A tubular set for conveying blood between a patient and a blood treatment apparatus, said set comprising the flow through bubble trap of claim 8.

14. An extracorporeal, flow-through bubble trap for blood lines, which comprises: a chamber-defining wall; a blood inlet and a blood outlet each comprising a tube spaced from said wall at intermediate portions thereof within said chamber, each tube extending from the top to the bottom of said chamber, each tube having an impermeable wall and extending through said chamber-defining wall to communicate with the interior of said chamber, said blood outlet connecting with said chamber interior adjacent the bottom thereof, said blood inlet tube having an aperture to direct blood horizontally into said chamber in directions facing away from said blood outlet, said chamber interior having a height which is no more than the longest horizontal dimension of said chamber interior, whereby said blood flow in the chamber is primarily horizontal, the volume of said chamber interior being no more than about 25 cc.

15. The bubble trap of claim 14 in which the blood outlet and inlet are horizontally separated at their closest points by at least about 8 mm.

16. The bubble trap of claim 14 in which said blood inlet comprises a tube that extends into said chamber interior at a position that is spaced at least 4 mm. from any chamber sidewall.

17. The bubble trap of claim 14, said chamber having a substantially oval cross section.

18. A tubular set for conveying blood between a patient and a blood treatment apparatus, said set comprising the flow through bubble trap of claim 14.

19. The method of passing blood through an extracorporeal, flow-through bubble trap for blood lines, which bubble trap comprises a chamber-defining wall, a blood inlet, and a blood outlet, said blood inlet comprising a tube that extends from the top to the bottom of said chamber within said chamber and further comprising a lateral aperture in said tube to communicate with the interior of the chamber, in which the blood outlet communicates with the chamber interior adjacent the bottom thereof, and the chamber interior has a top wall and a height that is less than 1.6 times the longest horizontal dimension of the chamber interior so that the blood flow in the bubble trap chamber is substantially horizontal, said method comprising: filling said chamber with blood to cause a substantial portion of the top wall of said chamber to be in continuous contact with said blood, and passing blood into said blood inlet and out of said blood outlet to cause bubbles to be removed from said blood and to collect directly underneath said top wall.

20. The method of claim 19 in which the flow rate of blood through said chamber is at least about 450 ml. per minute.

21. The method of claim 20 in which the volume of said chamber is no more than about 25 cc.

22. The method of claim 21 in which the horizontal cross section of said chamber is substantially oval, and said blood outlet draws blood from said chamber at a location adjacent the bottom thereof at a position opposed along the major axis of said cross section to the position of said blood inlet.

23. The method of claim 22 in which the height of said chamber interior is no more than the longest horizontal dimension of said chamber interior.

24. An extracorporeal, flow-through bubble trap for fluid flow lines, which comprises: a chamber-defining wall; a flow inlet and a flow outlet each extending through said wall to communicate with the interior of said chamber, at least said flow outlet communicating with the chamber interior adjacent the bottom thereof, said flow inlet and flow outlet being positioned adjacent to opposed lateral sides of said chamber, said flow inlet having a flow impermeable wall and a side aperture for directing fluid flow into said chamber exclusively in directions facing horizontally away from said flow outlet.

25. The bubble trap of claim 24 in which said flow outlet comprises a tube projecting into said chamber, said tube receiving fluid flow from said chamber only from directions facing horizontally away from said flow inlet.

26. The bubble trap of claim 25 in which the volume of said chamber interior is no more than about 25 cc.

27. The bubble trap of claim 26 in which said flow inlet and outlet are horizontally separated at their closest points by at least about 8 mm.

28. The bubble trap of claim 27 in which said flow inlet comprises a tube that extends into said chamber interior at a position that is spaced at least 4 mm. from any chamber sidewall.

29. The bubble trap of claim 28 in which said flow inlet and said flow outlet each comprise tubes that extend from the top to the bottom of said chamber in contact with top and bottom walls of said chamber.

30. The bubble trap of claim 24 in which said flow inlet comprises a tube that extends into said chamber interior at a position that is spaced at least 4 mm. from any chamber sidewall.

31. The bubble trap of claim 24 in which said chamber interior has a height which is no more than the longest horizontal dimension of said chamber interior, so that said fluid flow in the chamber is substantially horizontal.

32. The bubble trap of claim 31 in which said flow inlet and said flow outlet, each comprise tubes within the chamber that extend from the top to the bottom of said chamber.

33. The bubble trap of claim 31 in which said flow inlet comprises a tube that extends from the top to the bottom of said chamber, said tube defining a side aperture for fluid outlet adjacent to the bottom of said chamber.

34. The bubble trap of claim 24 in which said flow inlet and said flow outlet each comprise tubes within the chamber that extend from the top to the bottom of said chamber.

35. The bubble trap of claim 24 in which said flow inlet comprises a tube that extends from the top to the bottom of said chamber, said tube defining a side aperture for said flow outlet adjacent to the bottom of said chamber.

36. A tubular set for conveying blood between a patient and a blood treatment apparatus, said set comprising the flow through bubble trap of claim 14.

* * * * *